United States Patent
Higuchi et al.

(12)

(10) Patent No.: US 6,294,526 B1
(45) Date of Patent: Sep. 25, 2001

(54) USE OF FLAVONE DERIVATIVES FOR INDUCTION OF β-LACTAM-SENSITIVITY OF MRSA

(75) Inventors: Tomihiko Higuchi, Tokushima-ken; Yoichi Sato; Shoji Murasugi, both of Gifu-ken, all of (JP)

(73) Assignee: Alps Pharmaceutical Ind. Co., Ltd., Gifu-ken (JP)

( * ) Notice: Subject to any disclaimer, the term of this patent is extended or adjusted under 35 U.S.C. 154(b) by 0 days.

(21) Appl. No.: 09/121,681

(22) Filed: Jul. 23, 1998

(30) Foreign Application Priority Data

Feb. 6, 1998 (JP) .................................. 10-063834
Feb. 6, 1998 (JP) .................................. 10-063843

(51) Int. Cl.$^7$ .................................. A61K 31/43
(52) U.S. Cl. .................. 514/192; 514/197; 514/210; 514/310; 514/450; 514/451
(58) Field of Search .................................. 514/161, 192, 514/210, 724, 310, 451, 197, 450

(56) References Cited

U.S. PATENT DOCUMENTS 4,238,483 * 12/1980 Frazier .................................. 424/180
5,776,919 * 7/1998 Sukigara et al. ...................... 514/161

OTHER PUBLICATIONS

Sato, Y., et al., The 70$^{th}$ Annual Meeting of the Japanese Pharmaceutical Society, Sep. 25, 1997, Biochemical, vol. 69, No. 7, p. 911, Abstract 4956, 1997 (including English translation).

* cited by examiner

Primary Examiner—Elli Peselev

(57) ABSTRACT

A novel screening system for detecting a non-antibiotic compound having β-lactam-sensitivity-inducing activity comprising a non-antibiotic compound and a β-lactam antibiotic two times serially diluted series and a pharmaceutical composition having anti-MRSA activity comprising a flavone derivative and a β-lactam antibiotic.

15 Claims, No Drawings

USE OF FLAVONE DERIVATIVES FOR INDUCTION OF β-LACTAM-SENSITIVITY OF MRSA

TECHNICAL FIELD

The invention relates to a novel screening system for detecting chemical compounds which induce sensitivity to β-lactams in β-lactam resistant bacteria such as methicillin-resistant *Staphlococcus aurous* (MRSA) and, a pharmaceutical composition having anti-MRSA activity which comprises a flavone derivative selected by the screening system and a β-lactam, a method of increasing antibacterial activity of a β-lactam and a method of preventing and treating bacterial infectious diseases.

BACKGROUND OF THE INVENTION

The first antibiotic, penicillin, has a β-lactam ring and showed an eminent efficacy against staphylococci. However, staphylococci can easily produce penicillinase (i.e., β-lactamase) to inactivate penicillin. The staphylococci is called as penicillin-resistant bacteria. Against penicillin-resistant bacteria, for example, penicillinase-resistant penicillin- and cephem- antibiotics were developed and the problem involving penicillin-resistant bacteria seemed to be almost solved. However, a MRSA against which all β-lactams have no effect developed.

The MRSA is widely resistant not only to penicillin-antibiotics but also to cephem- and aminoglycoside- antibiotics. Recently, as a result of overuse of cephem antibiotics of the third generation cephems which are weakly antibacterial to *Staphylococcus aureus*, the cephem-resistant *Staphylococcus aureus* selectively proliferated and spread in hospitals, and therefore, the cephem-resistant *Staphylococcus aureus* has become a serious object of public concern as infectious bacteria in hospitals. Vancomycin (VCM) or the like is currently used as an anti-bacterial agent against MRSA-infectious diseases; however, problems are that the sterilizing power of VCM is not very potent over a short duration and VCM has severe side effects such as ototoxicity and nephrotoxicity.

In order to promote anti-bacterial activity against MRSA, combinations of plural anti-bacterial agents have been studied, for example, a combination of an aminoglycoside and β-lactam or a phosphomycin and a β-lactam has been tried, however the effectiveness of the combinations is not sufficient.

Novel anti-bacterial agents are urgently needed to be developed that are based on a novel mechanism of function different from conventional mechanisms and effective against MRSA.

SUMMARY

While the present inventors were researching an herb medicine having no or less side effects and also anti-MRSA activity, they found that apigenin, luteolin and flavone derivatives having chemical structures similar thereto have anti-MRSA activity. It has also been found that the flavone derivatives inhibit β-lactam-resistance of MRSA and induce sensitivity to β-lactam in MRSA. The present invention has been achieved based on the above findings.

The invention relates to a novel screening system for detecting chemical compounds which induce sensitivity to β-lactams in β-lactam resistant bacteria such as MRSA.

Many combinations of plural antibiotics were studied, however as yet no combination of a non-antibiotic and a β-lactam has been reported.

Therefore, in a first embodiment, the present invention provides a novel screening system for detecting a non-antibiotic compound having β-lactam-sensitivity-inducing activity comprising a β-lactam antibiotic and a non-antibiotic compound suspected to be effective to induce sensitivity.

In a second embodiment, the present invention provides a pharmaceutical composition having anti-MRSA activity which comprises a β-lactam antibiotic and the non-antibiotic compound detected by the screening system to be effective to induce sensitivity or a pharmaceutically acceptable salt thereof. The non-antibiotic compounds may be liavone derivatives. The pharmaceutical composition may increase anti-bacterial activity of a β-lactam antibiotic. The antibacterial activity may be against MRSA.

A third embodiment is a method for increasing antibacterial activity of a β-lactam antibiotic which comprises adding a flavone derivative to the β-lactam antibiotic.

A fourth embodiment is a method for treating or preventing an infectious disease of which the source of infection is *Staphylococcus aureus* or methicillin-resistant *Staphylococcus aureus* which comprises administering a flavone derivative together with the β-lactam antibiotic.

Apigenin or luteolin, which were selected by the screening system of the present invention, are found in the whole grass of *Scutellaria barbata* D. Don. *Scutellaria barbata* is a perennial plant of (Labiatae) and further includes alkaloids, flavonoid glycosides, polyphenol and furalols.

The dried whole grasses of Scutellaria barbata were almost stripped of leaves down to stems with flower petals and shoots. They are 5–25 cm in length, square. The surface of the stems is yellowish green or purplish brown, lustrous and smooth. Their medical activities have been mentioned as being antipyretic, antidotal, hemostyptic, and analgetic activities. However, It has not been reported that Scutellaria barbata has anti-MRSA activity or that flavone derivatives such as apigenin, and luteolin have anti-MRSA activity.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

Examples of β-lactam antibiotics useful herein include methicillin (DMPPC), oxacillin (MIPC), penicillin G (PCG), ampicillin (ABPC), cephalothin (CET), cefoxitin (CFX), cefuroxime (CXM) and cefotaxime (CTX). Examples of flavone derivatives useful herein include flavone, apigenin, luteolin, kaempferol, quercetin, sakuranetin, eriodictyol, (+)-taxifolin and phloretin.

The generic name or an abbreviation of an antibiotic referred to herein include both the free acid and pharmaceutically acceptable salts thereof. "Pharmaceutically acceptable salt" means a pharmaceutically acceptable salt of a β-lactam antibiotic which is conventionally used. As "a pharmaceutically acceptable salt", there may be exemplified salts such as sodium, potassium and calcium, an amine salt such as procaine, dibenzyl amine, and an addition salt such as hydrochloric acid salt.

The screening of the present invention may be carried out according to the agar plate dilution method designated by the Japan Society of Chemotherapy (Chemotherapy 29(1), 76–79 (1981)). Mueller-Hinton agar base semi-synthetic medium may be used for a plate culture medium for a sensitivity test together with an inoculating bacteria solution which may be prepared by culturing bacteria to be tested at 37° C. for 20 hours diluted with 8.5% by isotonic sodium chloride solution to $10^6$ CFU/ml. Diluted β-lactam solutions are prepared by two times serial dilution. 1 ml of the diluted β-lactam solution and 1 ml of a predetermined concentration of a sample to be tested are added to 8 ml of the plate culture medium for a sensitivity test. To the resultant plate culture medium for sensitivity test, the bacteria are inoculated using a microplanter (SAKUMASEISAKUSYO Co.), cultured for 20 hours at 37° C. followed by assessing for a minimum inhibition concentration (MIC). A minimum inhibition concentration means a minimum concentration at which growth of bacteria is completely inhibited.

Alternatively, the screening of the present invention may be carried out according to the broth microdilution method designated by the Japan Society of Chemotherapy (Chemotherapy 38(1), 102–105 (1990)). Muellar-Hinton broth is used as a culture medium for the sensitivity test, and 50 mg/ml of calcium(Ca) ion, 25 mg/ml of magnesium(Mg) ion, and 2% sodium chloride (NaCl) are added thereto. An inoculating bacteria solution may be prepared by culturing bacteria to be tested in Mueller-Hinton broth at 37° C. for 20 hours and diluting with Mueller-Hinton broth to $10^5$ CFU/ml final concentration of inoculating bacteria. Diluted β-lactam solution is prepared by two times serial dilution series. 10 μl of the diluted β-lactam solution and 10 μl of a predetermined concentration of a sample of bacteria to be tested are added to mix with 80 μl of the culture medium for the sensitivity test. To the resultant plate culture medium for sensitivity test, the inoculating bacteria are added and culturing is carried out for 20 hours at 37° C. and then assessment for a minimum inhibition concentration (MIC) is carried out. A minimum inhibition concentration means the minimum concentration of β-lactam at which growth of bacteria is not recognized by the naked eye.

In addition to the above two methods, the screening of the present invention may be carried out according to a crowded plate technique, a bacterial agar plate method, a spraying technique, a three-layered plate method, an agar-on-paper method, a replica plate method or a disc diffusion method and the like. In those methods, diluted β-lactam solution should be prepared by two times serial dilution and added to the culture medium for sensitivity testing to be subjected to the screening.

The sample to be subjected to the screening system is not limited to plant products. For example, crude drugs of land animal origin, insect origin and marine animal origin, or synthetic products and other products can be subjected to the screening system.

Any product which has been found useful for prophylaxis or treatment of MRSA can be formulated with a β-lactam as a pharmaceutical composition having anti-MRSA activity.

Purification of apigenin and luteolin which were found to be useful according to the screening system of the present invention. *Scutellaria barbata* D. Don (1.5 kg) was refluxed with 50% ethanol 2 hours and the hot solution was filtered by suction. The filtrate was concentrated under vacuum and ether was added thereto and extracted. An ether layer was concentrated to dryness at 70° C. under reduced pressure to give a brown and viscous product. The product was dissolved in absolute alcohol and the resultant solution was referred to as "ether extract". The ether extract was put on a glass column (70×20 mm) which was packed with silica gel (Kieselgel 60), and fractionated by n-hexane-ethyl acetate to give two fractions which showed antibacterial activity. The fractions were put on a glass column (40×75 mm) which was packed with ODS-Q3 (WAKO), and fractionated by 50% methanol to give two fractions having antibacterial activity. One of them was subjected to chromatography on LiChrosorb Si 60 (25×250 mm) and purified by chloroform-methanol (9:1) to give 920 mg of apigenin (SB-1) and the other fraction was purified by n-hexanβ-ethyl acetate (1:9) to give 25 mg of luteollin.

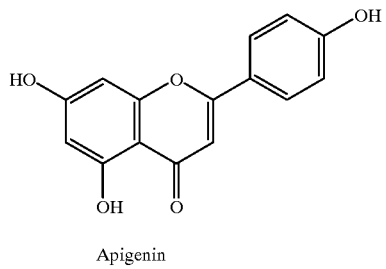

Apigenin

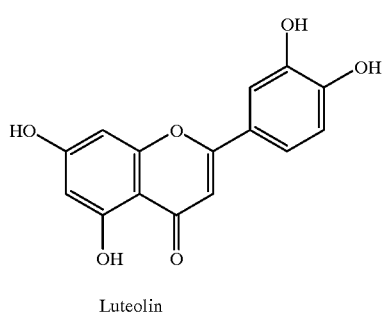

Luteolin

Pharmaco Experiments (A) Antibacterial activities of ether extract from *Scutellaria barbata*, SB-1 (isolated from *Scutellaria barbata*), apigenin (authentic sample) and luteolin (authentic sample) were shown in Table 1.

TABLE 1

| Strain No. | MIC (μg/ml) | | | |
| --- | --- | --- | --- | --- |
| | Ether Extract | SB-1 | Apigenin | Lutelin |
| 1 | 250 | 15.6 | 7.8 | 125 |
| 2 | 125 | 7.8 | 3.9 | 125 |
| 3 | 250 | 15.6 | 7.8 | 125 |
| 4 | 250 | 15.6 | 7.8 | 125 |
| 5 | 125 | 7.8 | 3.9 | 62.5 |
| 6 | 125 | 7.8 | 3.9 | 62.5 |
| 7 | 125 | 3.9 | 3.9 | 62.5 |
| 8 | 125 | 7.8 | 3.9 | 62.5 |
| 9 | 250 | 15.6 | 3.9 | 62.5 |
| 10 | 125 | 15.6 | 15.6 | 62.5 |
| 11 | >500 | >250 | >250 | 125 |
| 12 | >500 | >250 | >250 | 125 |
| 13 | 250 | 31.3 | 7.8 | 62.5 |
| 14 | 500 | 31.3 | 7.8 | 125 |
| 15 | 250 | 15.6 | 7.8 | 125 |
| 16 | 250 | 15.6 | 7.8 | 125 |
| 17 | 125 | 7.8 | 3.9 | 125 |
| 18 | >500 | >250 | >250 | 125 |
| 19 | >500 | >250 | >250 | 125 |
| 20 | 500 | 31.3 | 31.3 | 62.5 |
| 21 | 250 | 250 | >250 | 125 |
| 22 | 500 | 250 | >250 | 125 |
| 23 | 500 | 15.6 | 15.6 | 62.5 |
| 24 | 250 | 31.3 | 3.9 | 62.5 |
| 25 | 250 | 7.8 | 3.9 | 125 |
| 26 | 250 | 15.6 | 15.6 | 125 |
| 27 | 250 | 31.3 | 15.6 | 62.5 |

Strain Nos. 1 to 20 are MRSA and Nos. 21 to 27 are MSSA (Methicillin-sensitive *Staphylooccus aureus*).

Results

MIC values of ether extract from *Scutellaria barbata* against 20 strains of MRSA and 7 strains of MSSA rang from 125 to >250 μg/ml and showed high antibacterial activities. The antibacterial activities of isolated SB-1 and apigenin are on the same level with each other and their MIC values range from 3.9 to >250 μg/ml. Their MIC values against MRSA and MSSA are inconsistent and some of them showed strong activity (>250 μg/ml). Luteolin did not show difference between strains and its MIC values against both of MRSA and MSSA are almost fixed, and range from 62.5 to 125 μg/ml (see Table 1).

(B) The relation between chemical structures of flavones and their antibacterial activities were studied.

Antibacterial activity is determined for flavones including flavone, flavonol, flavanone, isoflavone, catechin and calchone, as follows:

Flavones are flavone, chrysin, acacetin and baicalein; flavonols are kaempferol, quercetin, rhamnetin, myricetin and quercetagetin; flavanones are liquiritigenin, sakranetin, naringenin, hesperetin and eriodictyol; isoflavones are (+)-taxifolin, formononetin, daidzein and genistein; catechin is (+)-catechin; and calchone is phloretin.

Flavones were dissolved in methanol and the others were dissolved in 0.1 N NaOH. A method for determination of antibacterial activity is, as described above, an agar plate dilution method designated by the Japan Society of Chemotherapy (Chemotherapy 29(1), 76–79 (1981)) to determine MIC value. $MIC_{80}$ is a concentration at which a strain is prohibited to proliferate by 80% and $MIC_{50}$ is a concentration at which a strain is prohibited to proliferate by 50%.

The results were shown in Table 2 as follows:

TABLE 2

Antibacterial activity of flavone derivatives against MRSA and MSSA

| Compound | MRSA (20 strains) | | | MSSA (7 strains) | | |
| --- | --- | --- | --- | --- | --- | --- |
| | MIC | $MIC_{50}$ | $MIC_{80}$ | MIC | $MIC_{50}$ | $MIC_{80}$ |
| [1] Flavones | | | | | | |
| Flavone | >250 | >250 | >250 | >250 | >250 | >250 |
| Chrysin | >250 | >250 | >250 | >250 | >250 | >250 |
| Apigenin | 3.9–>250 | 7.8 | 31.3 | 3.9–>250 | 15.6 | >250 |
| Acacetin | >250 | >250 | >250 | >250 | >250 | >250 |
| Baicalein | >250 | >250 | >250 | >250 | >250 | >250 |
| Luteolin | 62.5–125 | 125 | 125 | 62.5–125 | 125 | 125 |
| [2] | | | | | | |
| Kaempferol | 250–>250 | 250 | 250 | 250–>250 | 250 | 250 |
| Quercetin | 125–>250 | 250 | 250 | 250–>250 | 250 | >250 |
| Rhamnetin | >250 | >250 | >250 | >250 | >250 | >250 |
| Myricetin | 250–>250 | >250 | >250 | >250 | >250 | >250 |
| Quercetagetin | >250 | >250 | >250 | >250 | >250 | >250 |
| [3] | | | | | | |
| Liquiritigenin | 250–>250 | >250 | >250 | 250–>250 | >250 | >250 |
| Sakranetin | 125–>250 | 125 | >250 | 125–>250 | >250 | >250 |
| Naringenin | >250 | >250 | >250 | >250 | >250 | >250 |
| Hesperetin | >250 | >250 | >250 | >250 | >250 | >250 |
| Eriodictyol | 250 | 250 | 250 | 250 | 250 | 250 |
| [4] | | | | | | |
| (+)-Taxifolin | >250 | >250 | >250 | >250 | >250 | >250 |
| [5] | | | | | | |
| Formononetin | >250 | >250 | >250 | >250 | >250 | >250 |
| Daidzein | >250 | >250 | >250 | >250 | >250 | >250 |
| Genistein | >250 | >250 | >250 | >250 | >250 | >250 |
| [6] | | | | | | |
| (+)-Catechin | >250 | >250 | >250 | >250 | >250 | >250 |
| Phloretin | 125–>250 | 250 | 250 | 125–250 | 125 | 250 |

Results

Kaempferol, quercetin, sakranetin, eriodictyol and phioretin in addition to apigenin and luteolin showed antibacterial activity, however, their MIC values were not as strong as those apigenin and luteolin and in each case were 250 μg/ml (see Table 2).

(C) The relation between expression of activity and chemical structure is summarized as follows:

Among the flavones, only apigenin and luteolin and among the flavonols, only kaemferol and quercetin showed activity, respectively. Consequently, hydroxy groups at 5-, 7- and 4'- positions appear to be important for the expression of activity. None of the dihydroflavonolo, isoflavones and a catechin showed any activity, but phloretin of a calchone showed activity, and therefore, stereochemical structure of a flavone and position of a hydroxy group may be involved with the expression of activity.

MRSA is resistant to many chemotherapeutic agents and use of many kinds of chemotherapeutics at the same time has been tried.

It has now been found that addition of an amount of apigenin to less than the MIC of apigenin could improve antibacterial effect of methicillin on MRSA in a culture medium.

That is, $MIC_{50}$ of methicillin alone is 1000 μg/ml; however, when 4 μg/ml of apigenin was added to methicillin, the $MIC_{50}$ was 15.6 μg/ml, which was about 700 times as potent as for methicillin alone (Table 3).

(D) Then use of 4 μg/ml of apigenin and other antibiotics at the same time was studied. The antibiotics are penicillin, ampicillin, cephalothin, cefoxitin, cefuroxime, cefotaxime, vancomycin, streptomycin, chloramphenicol, kanamycin, erythromycin, nalixic acid and tetracycline.

Results

Only methicillin and cefoxitin inhibited β-lactam resistant MRSA under the presence of 4 μg/ml of apigenin (Table 3).

TABLE 3

|  | Antibiotics alone | | | Apigenin (4 μg/ml) | | |
| --- | --- | --- | --- | --- | --- | --- |
|  | MIC | $MIC_{50}$ | $MIC_{80}$ | MIC | $MIC_{50}$ | $MIC_{80}$ |
| Methicillin | 3.9–>250 | >250 | >250 | 0.98–>250 | 15.6 | 62.5 |
| Oxacillin | 0.98–>250 | 250 | >250 | 0.98–>250 | 250 | >250 |
| Penicillin G | 0.49–125 | 31.3 | 62.5 | 0.49–62.5 | 15.6 | 62.5 |
| Ampicillin | 2.0–125 | 31.3 | 62.5 | 2.0–62.5 | 31.3 | 31.3 |
| Cephalothin | 0.98–250 | 125 | 250 | 0.98–250 | 125 | 125 |
| Cefoxitin | 2.0–>250 | 250 | >250 | 2.0–125 | 31.3 | 62.5 |
| Cefuroxime | 7.8–>250 | >250 | >250 | 7.8–>250 | >250 | >250 |
| Cefotaxime | 3.9–>250 | >250 | >250 | 2.0–>250 | >250 | >250 |
| Vancomycin | 0.98–2.0 | 0.98 | 0.98 | 0.49–0.98 | 0.49 | 0.98 |
| Streptomycin | 7.8–15.6 | 7.8 | 15.6 | 2.0–15.6 | 7.6 | 7.8 |
| Chloramphenicol | 2.0–62.5 | 7.8 | 15.6 | 3.9–31.3 | 7.8 | 7.8 |
| Kanamycin | 0.24–>250 | >250 | >250 | 2.0–>250 | 250 | >250 |
| Erythromycin | 0.12–>250 | >250 | >250 | 0.12–>250 | >250 | >250 |
| Nalidixic acid | 62.5–>250 | >250 | >250 | 62.5–>250 | >250 | >250 |
| Tetracycline | 0.24–250 | 0.98 | 125 | 0.49–250 | 0.98 | 250 |

(E) In addition, use of methicillin and 21 of chemical structure analogues of apigenin at the same time was studied.

Table 4 shows antibacterial activity of methicillin against MRSA (21 strains) and MSSA (7 strains) under the presence of flavone derivatives (21 of chemical structure analogues of apigenin).

TABLE 4

Antibacterial activity of methicillin against MRSA and MSSA in the presence of flavone derivatives (50/μg)

|  | MRSA (20 strains) | | | MSSA (7 strains) | | |
| --- | --- | --- | --- | --- | --- | --- |
| Compound | MIC | $MIC_{50}$ | $MIC_{80}$ | MIC | $MIC_{50}$ | $MIC_{80}$ |
| Methicillin [1] | 3.9–>250 | >250 | >250 | 0.98–2.0 | 2.0 | 2.0 |
| Flavone | 0.49–125 | 3.9 | 62.5 | 0.98–2.0 | 0.98 | 2.0 |
| Chrysin | 3.9–>250 | >250 | >250 | 0.98–2.0 | 2.0 | 2.0 |
| Apigenin[a)] | 0.98–>250 | 15.6 | 62.5 | 0.98–2.0 | 0.98 | 2.0 |
| Acacetin | 3.9–>250 | >250 | >250 | 0.98–2.0 | 0.98 | 2.0 |
| Baicalein | 3.9–>250 | >250 | >250 | 0.98–2.0 | 2.0 | 2.0 |
| Luteolin [2] | 0.98–31.3 | 3.9 | 7.8 | 0.98–2.0 | 2.0 | 2.0 |
| Kaempferol | 2.0–>250 | 3.9 | 31.3 | 0.98–2.0 | 0.98 | 2.0 |
| Quercetin | 3.9–>250 | >250 | >250 | 0.98–2.0 | 2.0 | 2.0 |
| Rhamnetin | 3.9–>250 | >250 | >250 | 0.98–2.0 | 2.0 | 2.0 |
| Myricetin | 3.9–>250 | >250 | >250 | 0.98–2.0 | 2.0 | 2.0 |
| Quercetagetin [3] | 3.9–>250 | >250 | >250 | 0.98–2.0 | 2.0 | 2.0 |
| Liquiritigenin | 3.9–>250 | >250 | >250 | 0.98–2.0 | 2.0 | 2.0 |
| Sakranetin | 3.9–>250 | >250 | >250 | 0.98–2.0 | 2.0 | 2.0 |
| Naringenin | 3.9–>250 | >250 | >250 | 0.98–2.0 | 2.0 | 2.0 |
| Hesperetin | 2.0–>250 | >250 | >250 | 0.98–2.0 | 2.0 | 2.0 |
| Eriodictyol [4] | 2.0–>250 | >250 | >250 | 0.98–2.0 | 2.0 | 2.0 |
| (+)-taxifolin [5] | 2.0–>250 | 15.6 | >250 | 0.98–2.0 | 0.98 | 2.0 |
| Formononetin | 2.0–>250 | >250 | >250 | 0.98–2.0 | 2.0 | 2.0 |
| Daidzein | 3.9–>250 | >250 | >250 | 0.98–2.0 | 2.0 | 2.0 |

TABLE 4-continued

Antibacterial activity of methicillin against MRSA and MSSA in the presence of flavone derivatives (50/μg)

| Compound | MRSA (20 strains) | | | MSSA (7 strains) | | |
|---|---|---|---|---|---|---|
| | MIC | $MIC_{50}$ | $MIC_{80}$ | MIC | $MIC_{50}$ | $MIC_{80}$ |
| Genistein [6] | 3.9–>250 | >250 | >250 | 0.98–2.0 | 2.0 | 2.0 |
| (+)-Catechin [7] | 3.9–>250 | >250 | >250 | 0.98–2.0 | 0.98 | 2.0 |
| Phloretin | 0.98–>250 | 250 | >250 | 0.98–2.0 | 2.0 (μg/ml) | 2.0 |

[a)] 4 μg/ml

Results

Both of luteolin and kaemferol, which had showed independently antibacterial activity, inhibited resistance to methicillin in MRSA or MSSA at a MIC of 3.9 to 31.3 μg/ml. In addition, it is now surprisingly found that flavone and taxifoline, which had not independently showed antibacterial activity, also inhibited resistance to methicillin, among of them, flavone inhibited the most strongly and the $MIC_{50}$ of flavone is 3.9; μg/ml. Incidentally, the effect of inhibiting β-lactam resistance by flavones as above occurred on only MRSA, particularly, on MRSA No.5 (Table 4).

(F) Antibacterial activity of methicillin under the presence of flavone was strong on MRSA No.5, and therefore, the antibacterial activity of methicillin against MRSA No.5 was studied increasing concentration of flavone in bouillon (Table 5).

TABLE 5

Effect of flavone on antibacterial activity of methicillin against MRSA No. 5

| | Concentration of Flavone (mM) | | | | |
|---|---|---|---|---|---|
| Control | 0.11[a)] | 0.2 | 0.23[b)] | 0.5 | |
| >1000 | 1000 | 31.2 | 31.2 | 15.6 | (μM) |

[a)] 25 μg/ml
[b)] 50 μg/ml

Results

Antibacterial activity of methicillin against MRSA in the presence of 0.11 mM of flavone is not shown, however, the antibacterial activity in the presence of 0.2 mM of flavone is prominently shown. In proportion to increase of the concentration, the antibacterial activity of methicillin increased.

(G) Antibacterial activity of 6 β-lactams, that is, cephalothin, cefuroxime, cefotaxime, cefoxitin, streptomycin and vancomycin, against MRSA in the presence of 0.5 mM flavone was studied in bouillon.

TABLE 6

| Concentration of flavone (mM) | MIC (μM) | | | | | | | |
|---|---|---|---|---|---|---|---|---|
| | DMPPC | MCIPC | CET | CXM | CTX | CFX | SM | VCM |
| 0 | 1000 | 1000 | 500 | >1000 | 1000 | 1000 | — | — |
| 0.5 | 15.6 | 15.6 | 1.95 | 7.8 | 7.8 | <0.98 | <0.98 | <0.98 |

DMPPC: Methicillin,
MCIPC: Oxacillin,
CET: Cephalothin,
CXM: Cefuroxime,
CTX: Cefotaxime,
CFX: Cefoxitin,
SM: Streptomycin,
VCM: Vancomycin.

Results

The results were different from those of apigenin as shown in Table 3. The addition of flavone to β-lactams inhibited resistance of NRSA No.5, that is, cephalothin, cefuroxime and cefotaxime in the presence of flavone, in addition to methicillin and cefoxitin, showed inhibitory effect on resistance of MRSA No.5, particularly, cefoxitin showed the inhibitory effect remarkably. The inhibitory effect appeared not to be showed in antibiotics other than β-lactams, i.e. streptomycin and vancomycin (Table 6).

Effective dose and methods for administration

Flavone derivatives and compounds which have been found to be useful by the screening system of the present invention may be formulated as external remedies which have antibacterial effect. Sterilizing agents or antibacterial agents using the flavones of the present invention can be prepared by conventional methods. The flavones may be used by addition to commercial disinfectants such as a cresol solution, a cresol and soap solution, an aqueous phenol solution for disinfecting. An effective dose of the flavones in the sterilizing agents or antibacterial agents may range from 0.1 to 10% by weight or by volume. The sterillizing agents or antibacterial agents including the flavones are useful for sterillizing of instruments, excreta of patients and for deterging skin, mucous membrane or wounds.

Flavone derivatives and compounds which have been found to be useful by the screening system of the present invention may be administered in the same way as β-lactam antibiotics orally, parentally and externally, generally, injections are preferred. The injections are prepared by conventional methods and also by dissolving the flavones in appropriate vehicles such as distilled water, isotonic sodium chloride solution or the like. The flavones may be orally administered in different forms in combination with β-lactams, for example, in a form of tablets, capsules, tablets coated by sugar and the like, liquid solutions or suspensions Flavone derivatives and compounds which have been found to be useful by the screening system of the present invention may be used for treatment of human bacterial infectious diseases of which the source of infection is MRSA and the like in combination with β-lactam antibiotics. A total dose for administration of the flavones and β-lactam antibiotics depends on the β-lactam antibiotic or the proportion in a combination, age, weight, and condition of patients, administration route and the like. For example, in the case of administration to an adult of weight of 70 kg, the total dose ranges from 10 mg to 100 mg at 1 to 3 times a day. The total dose and the administration route may be changed so as to be most effective.

The weight proportion of using at the same time of combination of the flavones and the β-lactam may range widely. The proportion may be changed according to the infectious disease, seriousness of the disease and the β-lactam in the combination, and therefore, the proportion is not limited. The effectiveness of the present invention can be achieved by combination with a conventional dose of the β-lactam.

A pharmaceutical composition of the present invention is prepared by a conventional method and is administered in a pharmaceutically acceptable form. For example, a solid administration form may include a diluent such as lactose, dextrose. saccharose, cellulose, corn starch and potato starch; a lubricant such as silica, talc, stearic acid, magnesium stearate or calcium stearate, and/or polyethylene glycol; a binder such as starch, gum arabic, gelatin, methyl cellulose, carboxy methyl cellulose, carboxy methyl cellulose, polyvinyl pyrrolidine; a disintegrating agent such as starch, arginic acid, arginate, sodium glycolate starch; a forming agent; coloring matter; a sweetening agent; a moistening agent such as lecithin, polysorbate, lauryl sulfate; and generally non-toxic and pharmaceutically inactive materials which can be used in medicinal formulations.

The pharmaceutical preparations are prepared by known methods, for example, mixing, granulating, tabletting, sugar coating or coating.

In the case of non-oral administration, a suppository directed to apply the rectumx may be used; however, usually an injection is used. The injections may be given in the form of solution, in-shit solution, suspension and the like. The injection preparations are basically prepared by suitably sterilizing an active compound to directly put into a container.

Injection preparations are most simply, prepared by suitably sterilizing active ingredients and then mixing or separately making an injection preparation. A solution for injection may be prepared by dissolving an active compound into an appropriate medium to fill into and sealing up in an appropriate ample or vial. The medium is usually distilled water for injection, however, the medium used in the present invention is not limited thereto. The injection may include, if desired an analgesic such as procaine hydrochloride, xylocaine hydrochloride, acetic acid, benzyl alcohol, phenol and the like which have local anesthetic activity; a preservative such as benzyl alcohol, phenol, methyl or propyl praben, chlorobuthanol and the like; a buffer solution such as a sodium salt of succinic acid, acetic acid and phosphoric acid; further an additive such as an isotonic agent, a stabilizing agent, a solubilizing agent and the like.

EXAMPLES

Example 1 (Agar Plate Dilution Method)

Mueller-Hinton agar base semi-synthetic medium was used as a plate culture medium for the sensitivity test, and an inoculating bacteria solution was prepared by culturing bacteria to be tested at 37° C. for 20 hours and diluting with 8.5% by weight isotonic sodium chloride solution to a final concentration of $10^6$ CFU/ml. Methicillin was diluted in two-times serial dilutions starting from 10 mg/ml. 1 ml of the diluted methicillin solution and 1 ml of a sample in a concentration of 500 μg/ml to be tested were added to 8 ml of the plate culture medium for the sensitivity test. To the resultant plate culture medium for the sensitivity test, the inoculating bacteria were inoculated using a microplanter (SAKUMASEISAKUSYO Co.), cultured for 20 hours at 37° C. and then minimum inhibition concentration (MIC) was assessed. Minimum inhibition concentration means a concentration at which growth was completely inhibited and $MIC_{80}$ means a concentration at which growth was inhibited by 80%.

Example 2 (a micro dose of solution dilution method)

Muellar-Hinton broth was used as a culture medium for the sensitivity test, and 50 mg/ml of calcium (Ca) ion, 25 mg/ml of maqnesium (Mg) ion, 2% sodium chloride (NaCl) were added thereto. An inoculating bacteria solution was prepared by culturing bacteria to be tested with Mueller-Hinton broth at 37° C. for 20 hours and diluting with Mueller-Hinton broth to $10^5$ CFU/ml final concentration of inoculating bacteria. Diluted β-lactam solutions were prepared in two times serial dilutions starting from 10 mM. Ten microliters of the diluted β-lactam solution and 10 μl of 5 mM of flavone were mixed with 80 μl of the culture medium for the sensitivity test in a microplate having U-shaped wells and samples of bacteria to be tested were added thereto. The mixture was cultured 20 hours at 37° C. and then assessed for minimum inhibition concentration (MIC). Minimum inhibition concentration means minimum concentration of a β-lactum at which growth of bacteria is inhibited to the extent that bacteria is not recognized by the naked eye.

Example 3 (Disinfectant)

Apigenin 0.5 g was dissolved into 1000 ml of distilled water to give an disinfectant.

Examples 4 to 8 (Disinfectants)

Disinfectants were prepared as described in Example 3, except that luteolinr quercetin, sakranetin, eriodictyol and phloretin were used instead of apigenin.

Example 9 (Tablet)

According to a conventional method for preparing of tablets, 50 mg of apigenin, 50 mg of methicillin, 1 g of lactose, 300 mg of starch, 50 mg of methyl cellulose and 30 mg of talc were mixed to prepare 10 tablets and coated with sugar.

Example 10 to 13 (Tablets)

Tablets were prepared as described in Example 9, except that luteollin, kaemferol, flavone and (+)-taxifolin were used instead of apigenin.

Example 14 (Tablet)

According to a conventional method for preparing of tablets, 50 mg of flavone, 50 mg of sodium cefoxitin, 1 g of lactose, 300 mg of starch, 50 mg of methyl cellulose and 30 mg of talc were mixed to prepare 10 tablets and coated with sugar.

Examples 15 to 17 (Tablets)

Tablets were prepared as described in Example 14, except that sodium cephalothin, sodium cefroxime and sodium cefotaxime were used instead of sodium cefoxitin.

Example 18 (Injection)

Sterilized mixture of 500 mg and 500 mg of sodium cefoxitin was sealed in a sterillized vial. It is dissolved into isotonic sodium chloride solution to make an injection when it is used.

Example 19 to 21 (Injections)

Injections were prepared as described in Example 18, except that sodium cephalothin, sodium cefroxime and sodium cefotaxime were used instead of sodium cefoxitin.

Example 22 (Injection)

Sterillized mixture of 400 mg of flavone and 400 mg of sodium cefoxitin was dissolved into 20 ml of physiolosical saline and passed through a millipore filter of 0.22 $\mu$m. Then it was sealed in a glass bottle which had been previously sterillized to make an injection.

Examples 23 and 24 (Injection)

Injections were prepared as described in Example 22, except that sodium cephalothin, sodium cefroxime and sodium cefotaxime were used instead of sodium cefoxitin.

Effects of the Invention

Compounds which has been found by the screening system of the present invention show an activity to induce sensitivity to $\beta$-lactams in resistant bacteria such as MRSA and the like. The present invention provides novel pharmaceutical compositions comprising a combination of a non-antibiotic compound and a $\beta$-lactam, which is different from conventional antibacterial agents.

The invention being thus described, it will be obvious that the same may be varied in many ways. Such variations are not to be regarded as a departure from the spirit and scope of the invention, and all such modifications as would be obvious to one those skilled in the art are intended to be included to be included within scope of the following claims.

What is claimed is:

1. A method for increasing antibacterial activity of a $\beta$-lactam antibiotic against methicillin-resistant *Staphylococcus aureus* which comprises adding a flavone derivative selected from the group consisting of flavone, apigenin, luteohn, eriodictyol, phloretin and (+)-taxifoline to the $\beta$-lactam antibiotic in an amount effective to increase antibacterial activity of the $\beta$-lactam antibiotic against the methicillin-resistant *Staphylococcus aureus*.

2. A pharmaceutical composition comprising a $\beta$-lactam antibiotic and at least one flavone derivative selected from the group consisting of flavone, apigenin, luteolin, eriodictyol, phloretin and (+)-taxifoline, said flavone derivative being present in an amount effective to increase antibacterial activity of the $\beta$-lactam antibiotic against methicillin-resistant *Staphylococcus aureus*.

3. A method for treating an infectious disease of which the source of infection is methicillin-resistant *Staphylococcus aureus* which comprises administering a $\beta$-lactam antibiotic and a flavone derivative selected from the group consisting of flavone, apigenin, luteolin, eriodictyol phloretin and (+)-taxifoline, said flavone derivative being administered in an amount to increase antibacterial activity of the $\beta$-lactam antibiotic against the methicillin-resistant *Staphylococcus aureus*.

4. The method according to claim 1, in which said $\beta$-lactam antibiotic is methicillin or cefoxitin.

5. The method according to claim 1, in which said flavone derivative is selected from the group consisting of flavone and (+)-taxifoline.

6. The method according to claim 1, in which said flavone derivative is flavone.

7. The method according to claim 1, in which said $\beta$-lactam antibiotic is selected from the group consisting of methicillin, oxacillin, cephalothin, cefuiroxime, cefotaxime and cefoitin.

8. The pharmaceutical composition according to claim 2, in which said $\beta$-lactam antibiotic is methicillin or cefoxifin.

9. The pharmaceutical composition according to claim 2, in which said flavone derivative is selected from the group consisting of flavone and (+)-taxifoline.

10. The pharmaceutical composition according to claim 2, in which said flavone derivative is flavone.

11. The pharmaceutical composition according to claim 2, in which said $\beta$-lactam antibiotic is selected from the group consisting of methicillin, oxacillin, cephalothin, cefuroxime, cefotaxime and cefoxitin.

12. The method according to claim 3, in which said $\beta$-lactam antibiotic is methicillin or cefoxitin.

13. The method according to claim 3, in which said flavone derivative is selected from the group consisting of flavone and (+)-taxifoline.

14. The method according to claim 3, in which said flavone derivative is flavone.

15. The method according to claim 3, in which said $\beta$-lactam antibiotic is selected from the group consisting of methicillin, oxacillin, cephalothin, cefuroxime, cefotaxime and cefoxtin.

* * * * *

UNITED STATES PATENT AND TRADEMARK OFFICE
CERTIFICATE OF CORRECTION

PATENT NO. : 6,294,526 B1
DATED : September 25, 2001
INVENTOR(S) : Tomihiko Higuchi et al.

It is certified that error appears in the above-identified patent and that said Letters Patent is hereby corrected as shown below:

Column 14, claim 1,
Line 3, change "luteohn" to -- luteolin --.

Column 14, claim 7,
Line 32, change "cefoitin" to -- cefoxitin --.

Column 14, claim 8,
Line 34, change "cefoxifin" to -- cefoxitin --.

Signed and Sealed this

Twelfth Day of March, 2002

Attest:

Attesting Officer

JAMES E. ROGAN
Director of the United States Patent and Trademark Office